United States Patent
Narciso Martinez et al.

(10) Patent No.: US 9,717,885 B1
(45) Date of Patent: Aug. 1, 2017

(54) CATHETER STABILIZATION DEVICE

(71) Applicants: Luis Alberto Narciso Martinez, Caracas (VE); Maura Spizzo de Narciso, Caracas (VE)

(72) Inventors: Luis Alberto Narciso Martinez, Caracas (VE); Maura Spizzo de Narciso, Caracas (VE)

(*) Notice: Subject to any disclaimer, the term of this patent is extended or adjusted under 35 U.S.C. 154(b) by 294 days.

(21) Appl. No.: 14/341,946

(22) Filed: Jul. 28, 2014

(51) Int. Cl.
*A61M 5/32* (2006.01)
*A61M 25/02* (2006.01)

(52) U.S. Cl.
CPC ....... *A61M 25/02* (2013.01); *A61M 2025/024* (2013.01); *A61M 2025/0266* (2013.01)

(58) Field of Classification Search
CPC ............ A61M 25/02; A61M 2025/024; A61M 2025/0266; A61M 2025/028; A61M 16/0497; A61M 2025/0246; A61M 2025/0253; A61M 2025/026; A61M 2025/0273; A61M 2209/082; A61M 2209/088; A61M 5/1418; Y10S 128/26
See application file for complete search history.

(56) References Cited

U.S. PATENT DOCUMENTS

| | | | |
|---|---|---|---|
| 4,936,858 A | 6/1990 | O'Keeffe | |
| 5,876,003 A * | 3/1999 | Waagenaar | B60R 19/00 248/200 |
| 7,476,249 B2 | 1/2009 | Frank | |
| 7,875,074 B2 | 1/2011 | Chen et al. | |
| 8,007,531 B2 | 8/2011 | Frank | |
| 8,900,196 B2 * | 12/2014 | Andino | A61M 5/1418 604/174 |
| 8,974,421 B1 * | 3/2015 | Khalaj | A61M 25/02 604/174 |
| 2006/0167338 A1 | 7/2006 | Shfaram | |
| 2010/0217388 A1 | 8/2010 | Cohen et al. | |
| 2011/0009960 A1 | 1/2011 | Altman et al. | |
| 2011/0106249 A1 | 5/2011 | Becker | |
| 2012/0004723 A1 | 1/2012 | Mortarino et al. | |
| 2012/0158134 A1 | 6/2012 | Codori-Hurff et al. | |
| 2013/0253645 A1 | 9/2013 | Kerr et al. | |

* cited by examiner

*Primary Examiner* — Rebecca E Eisenberg
(74) *Attorney, Agent, or Firm* — H. John Rizvi; Gold & Rizvi, P.A.

(57) ABSTRACT

The invention refers to a stabilization device for attaching and securing a catheter to the skin of a patient in order to maintain the catheter correctly placed through a catheter insertion site. The stabilization device includes a catheter clipping element which is attached to an anti-allergic adhesive pad. The catheter clipping element includes a clipping body that ends in open arms for easy and convenient clipping and unclipping of a catheter, cannula, catheter or cannula terminal adapter, or the like. The clipping body is oriented outwards from the top surface of the pad in a transverse direction, a vertical direction, or both transversely and vertically, in order to facilitate clipping and unclipping. A longitudinal axis of the clipping body can be tilted towards the pad top surface in order to enhance stabilization and favor correct orientation of the catheter towards the insertion site.

20 Claims, 10 Drawing Sheets

CATHETER STABILIZATION DEVICE

FIELD OF THE INVENTION

The present invention relates to a stabilization device for stabilizing a catheter, a cannula or other medical equipment to the skin of a patient, and in particular, to a stabilization device comprising an adhesive sheet and a resilient protruding clip, wherein the clip includes a cavity for snugly receiving a catheter, cannula or other medical equipment connector or tube, the clip opening being arranged upwards, sideways or tilted to allow for easy insertion and removal of the catheter, cannula or other medical equipment.

BACKGROUND OF THE INVENTION

Medical devices known as catheters or cannulas (hereinafter referred to generally as catheters) are commonly used for administering medicines into the body or extracting body fluids from the body. Normally, a catheter comprises a thin tube to be inserted into the body, the tube ending in a connector, adapter, Y-termination or other applicable termination designed to remain outside the body and facilitate the coupling of a wide variety of external fluid removal or insertion devices such as a bag, a syringe or a bottle. Frequently, in order to facilitate insertion of the catheter into the body, the catheter is supplied with an applicator. For example, the catheter can be supplied with an internal needle with a sharpened tip extending outwardly from inside the catheter tube; once the needle tip punctures the skin, the catheter and needle are jointly and percutaneously inserted into the appropriate body part, and the needle is then gently pulled outward and removed from within the catheter so that one end of the catheter tube remains inside the body and the opposite end of the catheter, often including a terminal adapter, remains outside the body allowing for coupling of fluid removal or insertion devices.

For instance, intravenous catheters are generally used for extracting blood from a vein and, especially, for the administration of medicines or fluids to a vein. Peripheral venous catheters are the most commonly used intravenous catheters, providing access to peripheral veins on the arm, leg or hand. Central venous or arterial catheters for inserting or removing fluids from a central vein or artery, respectively, are also known in the art. In general, intravenous catheters are normally comprised of a thin flexible tube manufactured from a suitable plastic material, such as Teflon or the like, the tube ending in a terminal adapter for attaching an extension tube or other suitable medical device or apparatus. Normally, intravenous catheters are inserted into the vein with help of an internal syringe, which is removed once the catheter has been inserted and correctly placed. Intravenous catheters, and particularly peripheral venous catheters, should not restrict the patient from moving the arm, hand, leg or other body part to which the catheter is attached, while guaranteeing secure stabilization of the catheter onto the skin.

In another example, epidural catheters are commonly used in the anesthesiology field in order to provide access to the spine and allow for administration of epidural anesthesia. Similarly to intravenous catheters, epidural catheters generally comprise a thin, elongated flexible tube ending in a terminal adapter. The tube is inserted in the body and into the specific area of the spine with help of a relatively long internal syringe, which is removed once the catheter is set in place. The terminal adapter remains outside the body. A low resistance syringe or other applicable device may be attached to the terminal adapter and deliver anesthesia through the catheter tube into the patient's spine.

In general, once a percutaneous catheter is inserted, the catheter must be secured to the skin of the patient in order to prevent it from being inadvertently or undesirably pulled out, as sudden removal could cause significant adverse effects on the medical procedure being carried out on the patient and damages to the patient him/herself. Normally, the medical professional secures (stabilizes) the catheter to the skin of the patient by placing a medical tape over the catheter terminal adapter and onto the skin. More specifically, tape can be placed covering the terminal adapter practically in its entirety, such as in the event that the terminal adapter is cylindrical or slightly truncoconical. Alternatively, more sophisticated terminal adapters include two opposite side wings extending from a terminal adapter main body, the side wings providing a flat surface on which to attach the tape without compromising the terminal adapter main body.

The use of medical tape for catheter stabilizing presents significant drawbacks. In the first place, placing the tape on the catheter is time consuming and non-convenient to the healthcare provider. In addition, the tape must be removed in order to access, manipulate and replace the catheter, thereby requiring new tape to be attached once the catheter is ready for use or has been replaced. Frequent tape removal and fresh tape placement can cause irritation of the skin, thereby causing discomfort in the patient; in addition, repetitive un-taping and re-taping can contaminate the intravenous catheter insertion site with adhesive particles and increase the risk of infection in the insertion site.

Accordingly, there remains a need in the art to provide a catheter stabilization system and method that facilitates manipulation and removal of the catheter, saving medical professional time, causing no discomfort in the patient, and minimizing the risk of skin irritation, catheter or insertion site contamination, and insertion site infection. In addition, the catheter stabilization device should preferably allow the patient to move his-her arm or other body part and should remain attached to the skin regardless of whether the patient is moving or has moved said body part.

SUMMARY OF THE INVENTION

The present invention overcomes the deficiencies of the known art and the problems that remain unsolved by providing a stabilization device to safely and securely attach a catheter, cannula or other applicable medical equipment (hereinafter referred to generically as catheter, unless otherwise specified), to the skin of a patient in order to maintain the catheter correctly placed through a catheter insertion site. The stabilization device includes a catheter clipping element which is attached to an anti-allergic adhesive pad. The catheter clipping element includes a rigid but slightly flexible clipping body that ends in open arms for easy and convenient clipping and unclipping of a catheter, cannula, catheter or cannula terminal adapter, or the like. The clipping body is oriented outwards from the top surface of the pad in a transverse direction, a vertical direction, or both transversely and vertically, in order to facilitate clipping and unclipping. A longitudinal axis of the clipping body can be tilted towards the pad top surface in order to enhance stabilization and favor correct orientation of the catheter towards the insertion site. The stabilization device in accordance with the invention is capable of being conveniently used in operation rooms, emergency rooms, hospital rooms, ambulances or other applicable site where a patient requires subcutaneous fluid administration or body fluid extraction.

In accordance with one embodiment of the present invention, the invention consists of a catheter stabilization device comprising:

a pad, said pad having a planar configuration extending in longitudinal and transverse directions, said pad including a top surface and a bottom surface, said bottom surface including an adhesive material suitable for removably attaching said bottom surface to skin;

at least one catheter clipping element, comprising:

a base, attached to the pad top surface;

an elongated resilient clipping body protruding from said base, said clipping body comprising opposed clipping arms extending in a spaced-apart configuration and resiliently movable relative to one another, said arms comprising a clipping protrusion;

an internal space delimited between said arms and configured to partially receive a catheter, wherein said internal space is arranged along an internal space longitudinal axis and extends from a first catheter pass-through opening on a first end of said clipping body and a second catheter pass-through opening on an opposite second end of said clipping body, and wherein said internal space is accessible through an insertion opening disposed between opposite free ends of said arms and arranged in spatial communication with said opposed first and second catheter pass-through openings; wherein said insertion opening is oriented outwardly from said pad top surface, in accordance with a vector forming an angle from zero to 180 degrees with said pad top surface.

In a second aspect, the internal space longitudinal axis forms an angle other than zero with the planar pad top surface, in order to longitudinally orient a catheter towards an insertion site, or away from an insertion site if need be.

In another aspect, the catheter clipping element comprises an elongated stem extending from the base to the elongated resilient clipping body, supporting the elongated resilient clipping body at a certain distance from the base along a substantial portion of the body length.

In another aspect, the stem comprises a first end and an opposed second end, wherein said second end is taller than said first end, providing a simple yet effective solution for orienting the internal space longitudinal axis to form an angle other than zero with the planar pad top surface.

In another aspect, the elongated resilient clipping body is integrally formed with the stem and the base, providing a cost-effective and mechanically robust elongated resilient clipping body.

In another aspect, the stem is integrally formed with the base, and the elongated resilient clipping body is removably attached to the stem, allowing the elongated resilient clipping body to be removed without having to detach the pad from the patient's skin.

In another aspect, the insertion opening is arranged on a plane that is perpendicular to said pad top surface, and thus the elongated resilient clipping body is oriented sideways (transversely) allowing for catheter clipping without the need of exerting a downward force on the patient's skin.

In another aspect, the insertion opening is oriented in an outward direction comprising a lateral component in a lateral direction that is perpendicular to said longitudinal and transverse directions, the internal space therefore being oriented upwards or with an upward component relative to the pad top surface. Such an arrangement provides extremely easy catheter clipping and unclipping, which can be useful in critical situations such as during surgery or when providing emergency care.

In another aspect, the outward direction further comprises a longitudinal component in said longitudinal direction, the insertion opening thus being tilted forward or rearward relative to the pad to surface, in order to orient the catheter longitudinally towards or away from the skin.

In another aspect, the catheter stabilization device can include a single catheter clipping element.

In another aspect, the catheter stabilization device can include only two catheter clipping elements, such as for attaching opposite ends of a catheter extension element or tube.

In another aspect, the insertion openings of the two catheter clipping elements are arranged on respective planes that are perpendicular to said pad top surface, and the insertion openings are oriented facing one another. In other words, the two catheter clipping elements face one another transversely and clipping must be carried out from the inside. Such an arrangement reduces the risk of the catheter becoming accidentally or undesirably unclipped.

In another aspect, there being two faced catheter clipping elements, the internal space longitudinal axis of one catheter clipping element is directed towards the planar pad top surface, and the internal space longitudinal axis of the other catheter clipping element is directed away from the planar pad top surface. Thus, one end of a catheter can be clipped longitudinally oriented towards the skin, and an opposite end can be clipped longitudinally oriented away from the skin.

In another aspect, the insertion openings of the two catheter clipping elements are arranged on respective planes that are perpendicular to said pad top surface, and said insertion openings are oriented oppositely to one another. In other words, the two catheter clipping elements are transversely opposed to one another and clipping must be carried out from the outside. Such an arrangement facilitates clipping and unclipping.

In another aspect, there being two opposed catheter clipping elements, the internal space longitudinal axis of one catheter clipping element is directed towards the planar pad top surface, and the internal space longitudinal axis of the other catheter clipping element is directed away from the planar pad top surface. Thus, one end of a catheter can be clipped longitudinally oriented towards the skin, and an opposite end can be clipped longitudinally oriented away from the skin.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The illustrations included herein present several embodiments of a catheter stabilization device in accordance with the present invention. In the present document, except otherwise stated, the term "catheter" will be used to generically refer to any medical device consisting of a thin, flexible tube to be inserted into a patient's body for providing or removing fluids such as medicines or body fluids, the tube normally including a terminal end adapter or connector for attaching extension tubes or medical devices. In addition, the term "catheter" is also understood to comprise extension tubes designed to be attached to a catheter or cannula inserted in the body of a patient.

Figure 1:
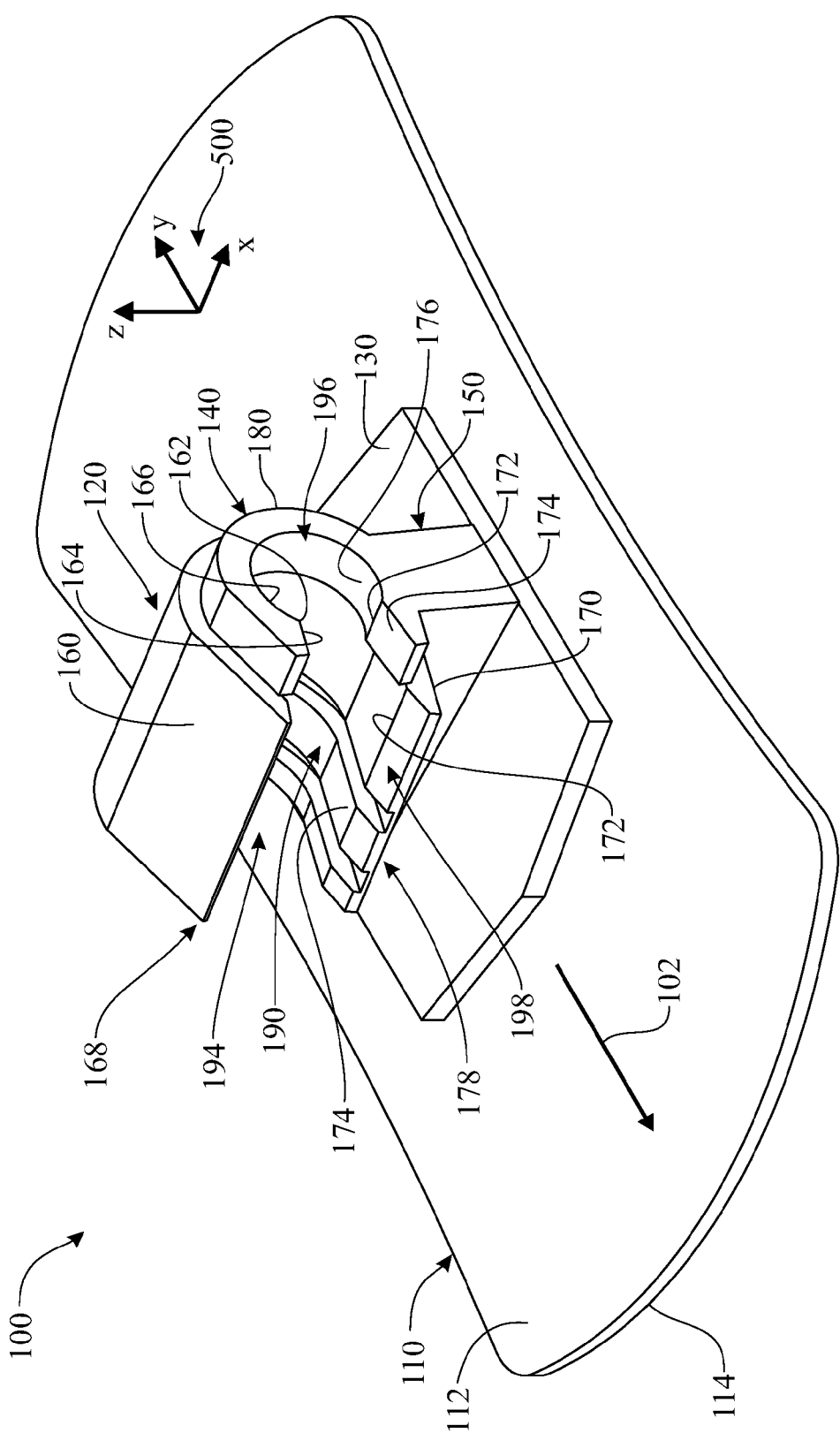
FIG. 1 presents an isometric view of a first embodiment of the stabilization device in accordance with the invention, comprising a single catheter clipping element having a transversely arranged insertion opening.

Referring initially to FIG. 1, a catheter stabilization device 100 in accordance with a first embodiment of the invention is presented in isometric view. An orthogonal isometric axis system 500 is also depicted, thereby defining a longitudinal direction X, a transverse direction Y and a lateral or vertical direction Z for further reference.

The catheter stabilization device 100 shown in the figure comprises an anti-allergic adhesive pad 110 configured to be attached to the skin of a human or animal patient. Pad 110 is arranged in a planar configuration, featuring a top surface 112 and an opposed bottom surface 114 in substantially parallel arrangement and perpendicular to vertical direction Z. Bottom surface 114 includes an anti-allergic adhesive material suitable for removably attaching the pad 110 to the skin. Bottom surface 114 will normally be initially covered by a peel-off paper or plastic sheet (not shown), to conceal and protect the adhesive material as known in the art.

Pad 110 further includes a catheter clipping element 120 for securing a catheter near the patient's skin. The catheter clipping element protrudes outwardly from the pad top surface 112, and comprises a base 130 and an elongated resilient clipping body 140. Base 130 is attached to pad top surface 112 by a heavy duty, traction- and torsion-resistive adhesive material that provides a relatively permanent connection between base 130 and catheter clipping element 120 throughout the useful lifetime of the catheter stabilization device 100. The elongated resilient clipping body 140, in turn, is arranged above and protruding outwardly from the base 130. In the present embodiment, an elongated stem 150 extends from the base 130 to the elongated resilient clipping body 140, allowing elongated resilient clipping body 140 to be arranged at a convenient distance from base 130.

Figure 2:
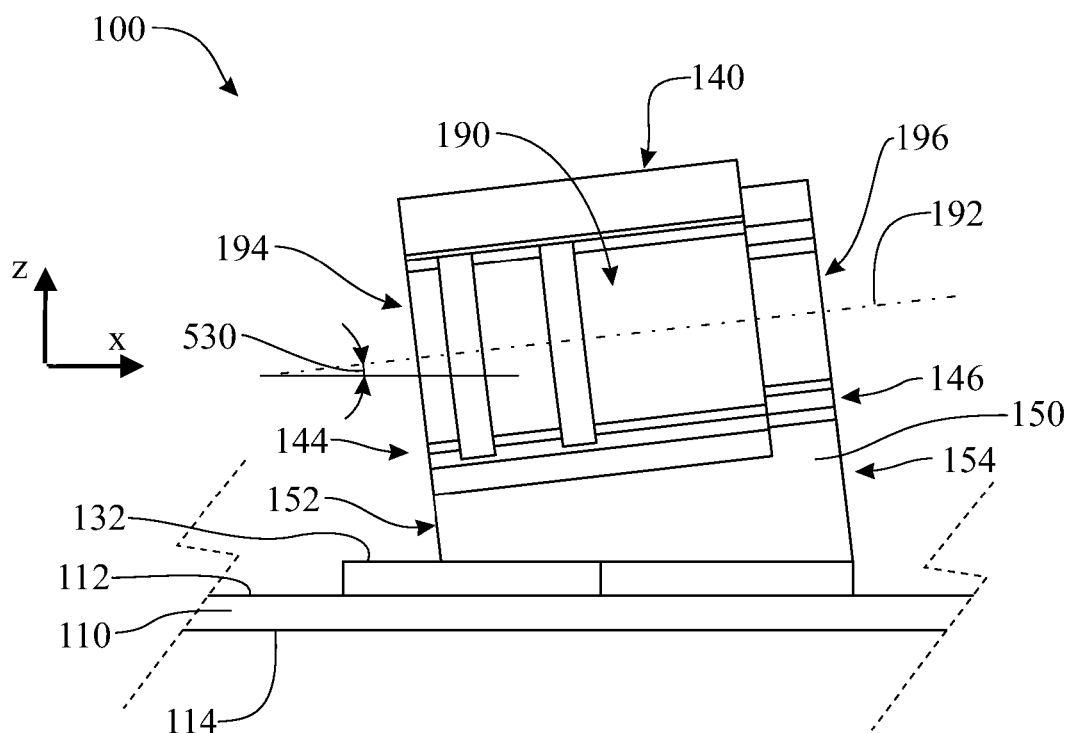
FIG. 2 presents a front elevation view of the stabilization device of FIG. 1.
Figure 3:
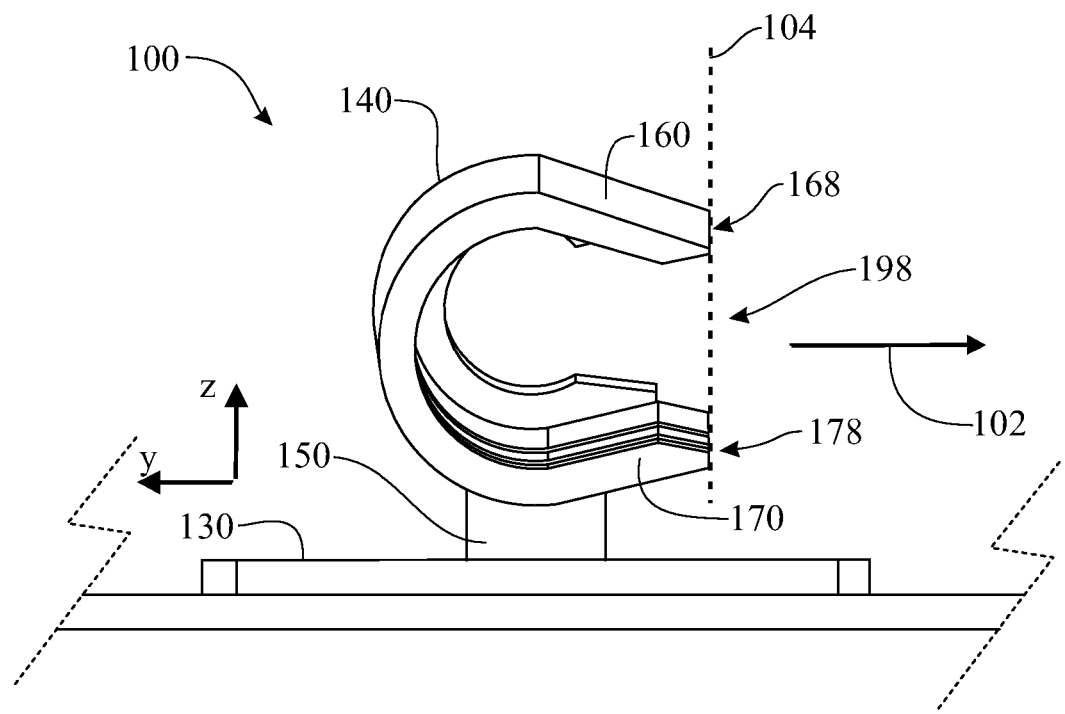
FIG. 3 presents a left side elevation view of the stabilization device of FIG. 1.

In accordance with the invention, the elongated resilient clipping body 140 comprises opposed clipping arms 160, 170 extending in a spaced-apart configuration and facing one another. In the present embodiment, the elongated resilient clipping body 140 is substantially C-shaped. A top clipping arm 160 extends from a rear wall portion 180 of the "C", whereas a bottom clipping arm 170 extends from stem 150. The clipping arms 160, 170 are resiliently movable relative to one another and are provided with several respective internal clipping protrusions 162, 172. In the present embodiment, the internal clipping protrusions 162, 172 are shaped as inwardly-oriented peaks between respective end tapered surfaces 164, 174 and respective internal concave surfaces 166, 176. In addition, the elongated resilient clipping body 140 comprises an internal space 190 delimited between the opposed clipping arms 160, 170 and configured to partially receive a catheter. The internal space 190 is arranged along an internal space longitudinal axis 192 (as best shown in FIG. 2) and extends from a first catheter pass-through opening 194 on a first end 144 of said clipping body and a second catheter pass-through opening 196 on an opposite second end 146 of said clipping body. An insertion opening 198 disposed on a side of elongated resilient clipping body 140 provides access to the internal space 190. The insertion opening 198 is arranged between opposite free ends 168, 178 of the clipping arms 160, 170, as best shown in FIG. 3. The first and second catheter pass-through openings 194, 196 are arranged in continuation of the insertion opening 198.

In accordance with the invention, the catheter clipping element insertion opening is oriented outwardly from the pad top surface. By oriented outwardly, it is understood that the catheter clipping element insertion opening is oriented in the direction of a vector that forms an angle from zero to 180 degrees with said pad top surface, i.e. that the catheter clipping element as per the invention is oriented vertically upward (in the lateral direction Z), horizontally (in a direction parallel to plane XY), or any combination thereof. Having an outwardly-oriented catheter clipping element has the effect of allowing a catheter to be inserted into or removed from the stabilization device without requiring removal of the stabilization device from the skin of the patient. Such effect provides several advantages. In the first place, patients are prevented from having to withstand the discomfort, irritation and uncleanliness caused by frequent un-taping and re-taping of stabilization devices. In addition, stabilizing, replacing or removing catheters from a patient's skin is less time-consuming in comparison with conventional tape-based stabilizing methods, thus allowing for a more efficient use of medical professional resources. Finally, catheters may be less-frequently replaced, further contributing to save time and material resources.

For example, in the embodiment shown in FIGS. 1 through 3, the insertion opening 198 is horizontally and transversely oriented, in accordance with a vector 102 parallel to the pad top surface 112 (and thus to the XY plane) and arranged at an angle of 180 degrees relative to transverse direction Y, as best shown in FIGS. 1 and 3. Thus, as best shown in FIG. 3, the insertion opening 198 is arranged on a plane 104 that is perpendicular to said pad top surface 112 (and to said vector 102). End tapered surfaces 164, 174 facilitate insertion of a catheter (tube, terminal end adapter, or other applicable part of a catheter, cannula or other medical equipment) through insertion opening 198. Insertion is carried out by placing a catheter (e.g., a tube, or a terminal adapter) proximal to the insertion opening 198 and exerting a force in an opposite direction to vector 102. Progressive contact between the catheter and the opposed arm end tapered surfaces 164, 174 will cause the top clipping arm 160 to slightly and resiliently separate from the bottom clipping arm 170, slightly opening the elongated resilient clipping body 140 allowing for the catheter to overcome the internal clipping protrusions 162, 172. Once the catheter is placed in the internal space 109, the resilient top clipping arm 160 returns to its original position producing a clicking effect, and the internal clipping protrusions 163 keep the catheter housed within the internal space 190.

Figure 4:
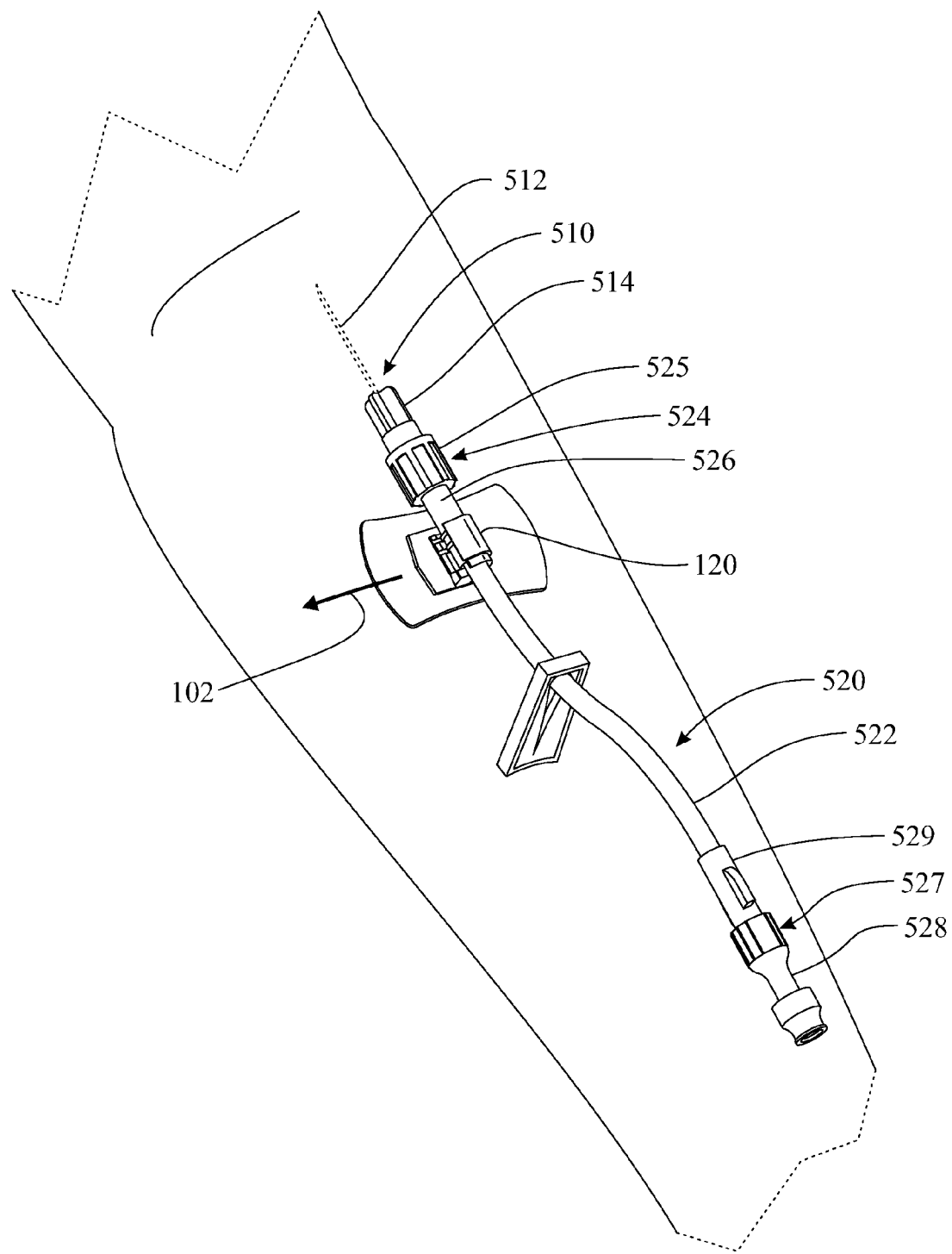
FIG. 4 presents the stabilization device of FIG. 1, shown in use, for stabilizing a catheter extension element attached to an intravenous catheter inserted into the left arm of a patient.

An example of such a transverse clipping connection is shown in FIG. 4, illustrating the catheter stabilization device 100 of FIG. 1 being used to stabilize a catheter placed on a patient's left forearm. As shown, a catheter 510 comprised of a thin flexible tube 512 and a terminal adapter 514 has been inserted into a patient's vein, the terminal adapter 514 remaining external to the patient's arm and adjacent to the skin. A catheter extension element 520, comprised of a flexible tube 522 terminated in a proximal terminal adapter 524 and a distal terminal adapter 527, is connected to the catheter 510. The proximal terminal adapter 524 includes a coupling head 525 and a rigid neck 526. In turn, the distal terminal adapter 527 includes a coupling head 528 and a rigid neck 529. The catheter extension element 520 is attached to the catheter 510 by having fastened the coupling head 525 to the catheter terminal adapter 514. As shown in the figure, the rigid neck 526 of the proximal terminal adapter 524 has been inserted in the catheter clipping element 120 in accordance with the invention by gently pushing the rigid neck 526 in a direction opposite to vector 102, until the rigid neck 526 has become clipped inside the catheter clipping element 120 as explained in the previous paragraph. If the medical professional were to remove the catheter, gently pulling the catheter extension element 520 transversely outward from the catheter clipping element 120, i.e. in the direction of vector 102 would cause the catheter extension element 520 to become unclipped.

The transversely-oriented catheter clipping element 120 of the present embodiment is particularly advantageous in that the catheter connector can be inserted in the clip without having to exert a vertically downward force component towards the patient's skin (i.e., a force in a direction opposite to lateral direction Z in accordance with FIG. 1). In addition, the catheter is particularly prevented from unclipping when the patient moves his arm or other body part, as insertion and removal of the catheter takes place in a direction that is orthogonal to the articulation plane of the joint (normally, plane XZ in accordance with FIG. 1).

The catheter stabilization device in accordance with the invention is preferably disposable. The pad can be manufactured in a relatively flexible material allowing the pad bottom surface to conform to the patient's body part on which it is attached; for instance, the pad can be a 3M™ or Avery Dennison™ medical pad, to name a few well-known commercial brands. In turn, the catheter clipping element is generally rigid but slightly flexible in order to provide the necessary clipping resiliency, and can be made, for instance and without limitation, of plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like, or combinations thereof.

In the embodiment shown in FIGS. 1 through 4, the internal space longitudinal axis 192 forms an angle 530 other than zero (as best shown in FIG. 2) with the planar pad top surface 112. Such an angled arrangement allows the catheter clipping element 120 to longitudinally orient the catheter towards the patient's skin, further contributing to maintain the catheter in its correct position and prevent the catheter, particularly the part of the catheter that is nearest to the insertion site (skin puncture) from moving undesirably. Preferably, as best shown in FIG. 2, this angled arrangement between the internal space longitudinal axis 192 and the pad 110 is achieved by providing the stem 150 with a first end 152 and an opposed second end 154, where the second end 154 is taller than the first end 152.

In the present embodiment, elongated resilient clipping body 140 is integrally formed with stem 150 and base 130, for instance by injection molding the entire catheter clipping element 120 in a single injection molding phase, providing a mechanically robust and cost-effective solution.

In alternative embodiments, the stem can be integrally formed with the base, whereas the elongated resilient clipping body can be removably attached to the stem. Removable attachment can be achieved by a thread, a male-female snap-on connection, a clip, or other applicable mechanical fastening means commonly known in the art. A removably attached elongated resilient clipping body is advantageous in that it can be easily and quickly replaced, if needed, without having to detach the entire catheter stabilization device from the patient's skin.

The illustrations of FIGS. 5 through 8 present a second embodiment the invention, consisting in a catheter stabilization device 200 having a pad 210 to which two catheter clipping elements 220*a*, 220*b* are attached. Similarly to the embodiment of FIG. 1, the pad 210 has a planar configuration and includes a top surface 212 and a bottom surface 214; the bottom surface 214 is provided with an adhesive material suitable for removably attaching the bottom surface 214 to skin.

Figure 5:
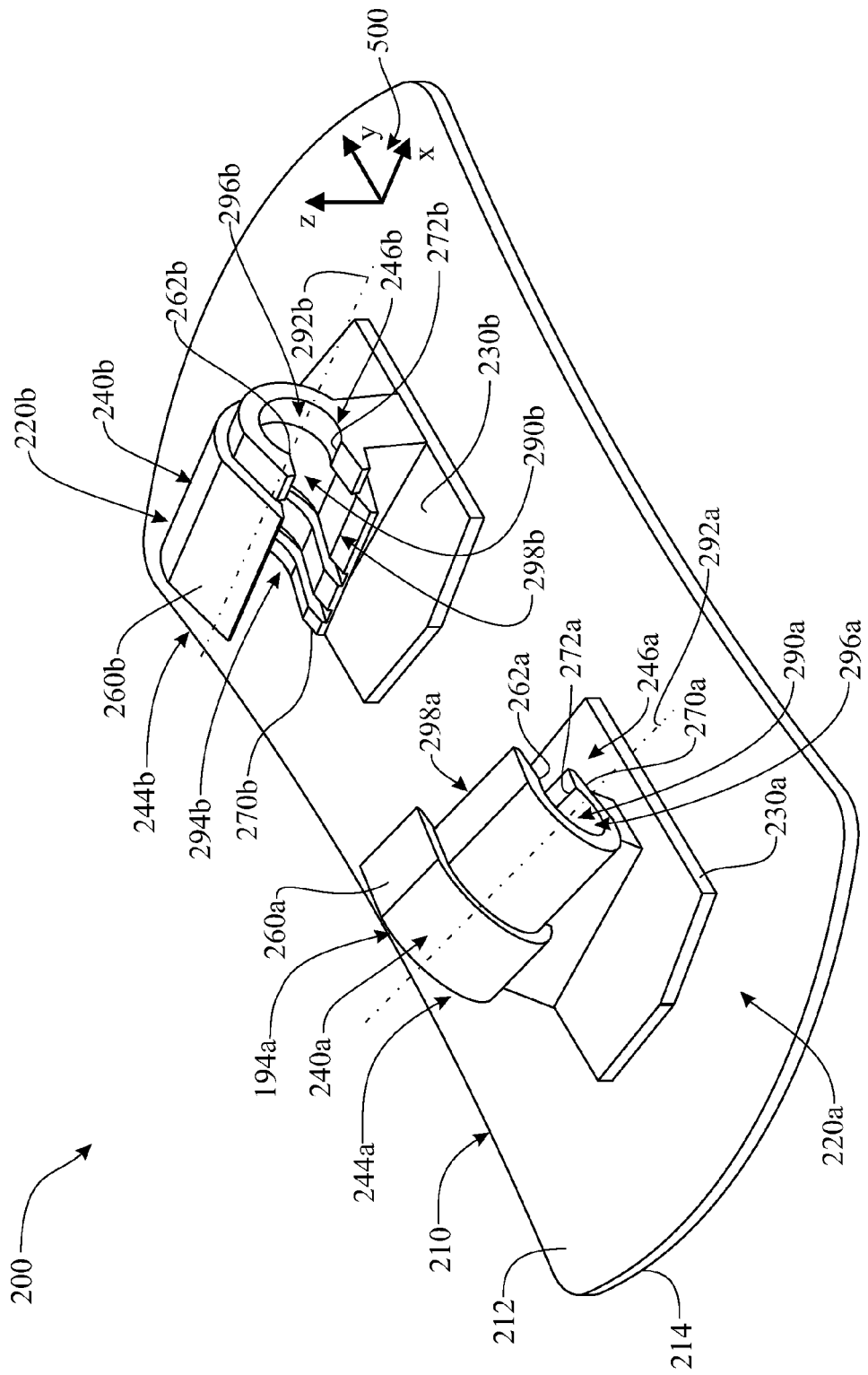
FIG. 5 presents an isometric view of another embodiment of the stabilization device in accordance with the invention, comprising two catheter clipping elements having transversely-arranged insertion openings facing one another.
Figure 6:
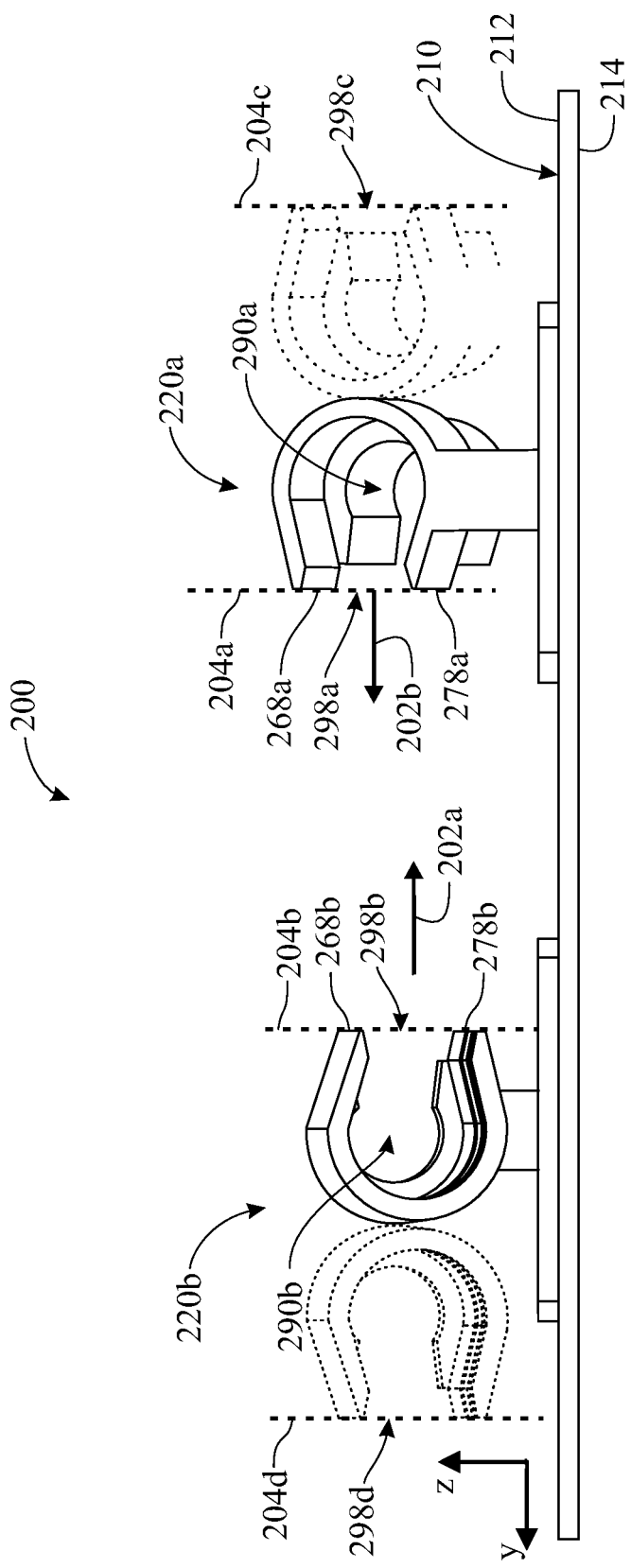
FIG. 6 presents a left side elevation view of the stabilization device of FIG. 5.

As best shown in FIGS. 5 and 6, each catheter clipping element 220a, 220b presents a base 230a, 230b, attached to the pad top surface 212, and an elongated resilient clipping body 240a, 240b protruding outwardly from the base 230a, 230b. The elongated resilient clipping bodies 240, 240b are composed of respective pairs of opposed clipping arms 260a, 270a; 260b, 270b. The clipping arms 260a, 270a of the leftmost catheter clipping element 220a (in accordance with the position of FIG. 5) extend in a spaced-apart configuration and resiliently movable relative to one another, and comprise an internal clipping protrusion 262a, 272a. Similarly, the clipping arms 260b, 270b of the opposite catheter clipping element 220b extend in a spaced-apart configuration and resiliently movable relative to one another, and comprise an internal clipping protrusion 262b, 272b. Each catheter clipping element 220a, 220b comprises a respective internal space 290a, 290b delimited between said respective pair of clipping arms 260a, 270a; 260b, 270b and configured to partially receive a catheter (i.e. a portion of catheter). As best shown in FIG. 5, the internal space 290a of the leftmost catheter clipping element 220a is arranged along an internal space longitudinal axis 292a and extends from a first catheter pass-through opening 294a on a first end 244a of said elongated resilient clipping body 240a and a second catheter pass-through opening 296a on an opposite second end 246a of said elongated resilient clipping body 240a. Similarly, the internal space 290b of the opposite catheter clipping element 220b is arranged along an internal space longitudinal axis 292b and extends from a first catheter pass-through opening 294b on a first end 244b of said elongated resilient clipping body 240b and a second catheter pass-through opening 296b on an opposite second end 246b of said elongated resilient clipping body 240b. As best shown in FIG. 6, presenting a side view of the device, the internal space 290a, 290b of each catheter clipping element 220a, 220b is accessible through a corresponding insertion opening 298a, 298b disposed between opposite free ends 268a, 278a; 268b, 278b of the corresponding pair of clipping arms 160a, 170a; 160b, 170b. Each internal space 290a, 290b is arranged in spatial communication with the corresponding opposed first and second catheter pass-through openings 294a, 296a; 294b, 296b. In addition, each insertion opening 298a, 298b is oriented outwardly from the pad top surface 212, in accordance with a vector forming an angle from zero to 180 degrees with said pad top surface 212. Specifically, the insertion openings 298a, 298b are oriented in accordance with respective horizontal vectors 202a, 202b parallel to said pad top surface 212.

Figure 7:
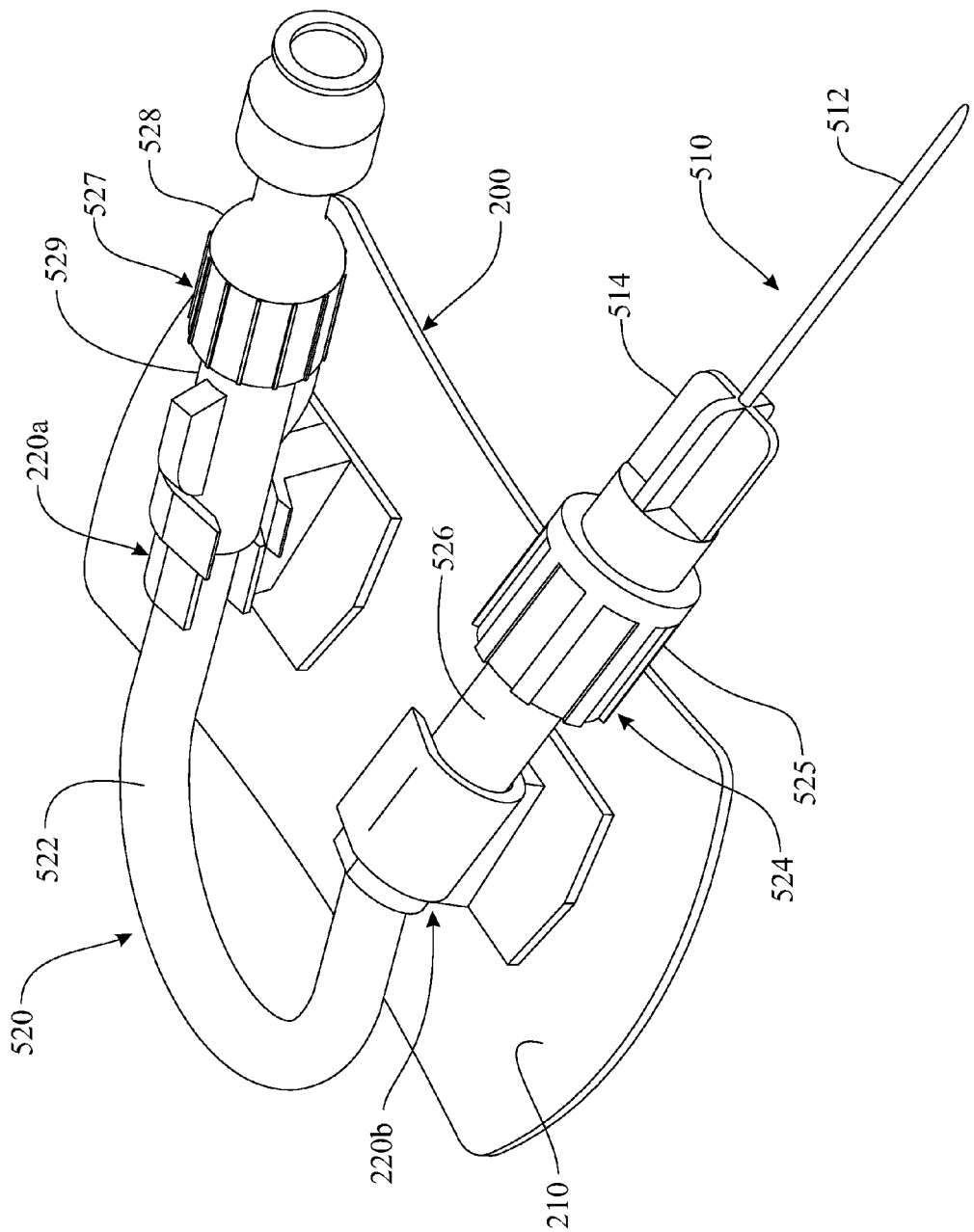
FIG. 7 presents an isometric view of the stabilization device of FIG. 5, to which a catheter extension element and an intravenous catheter have been assembled.
Figure 8:
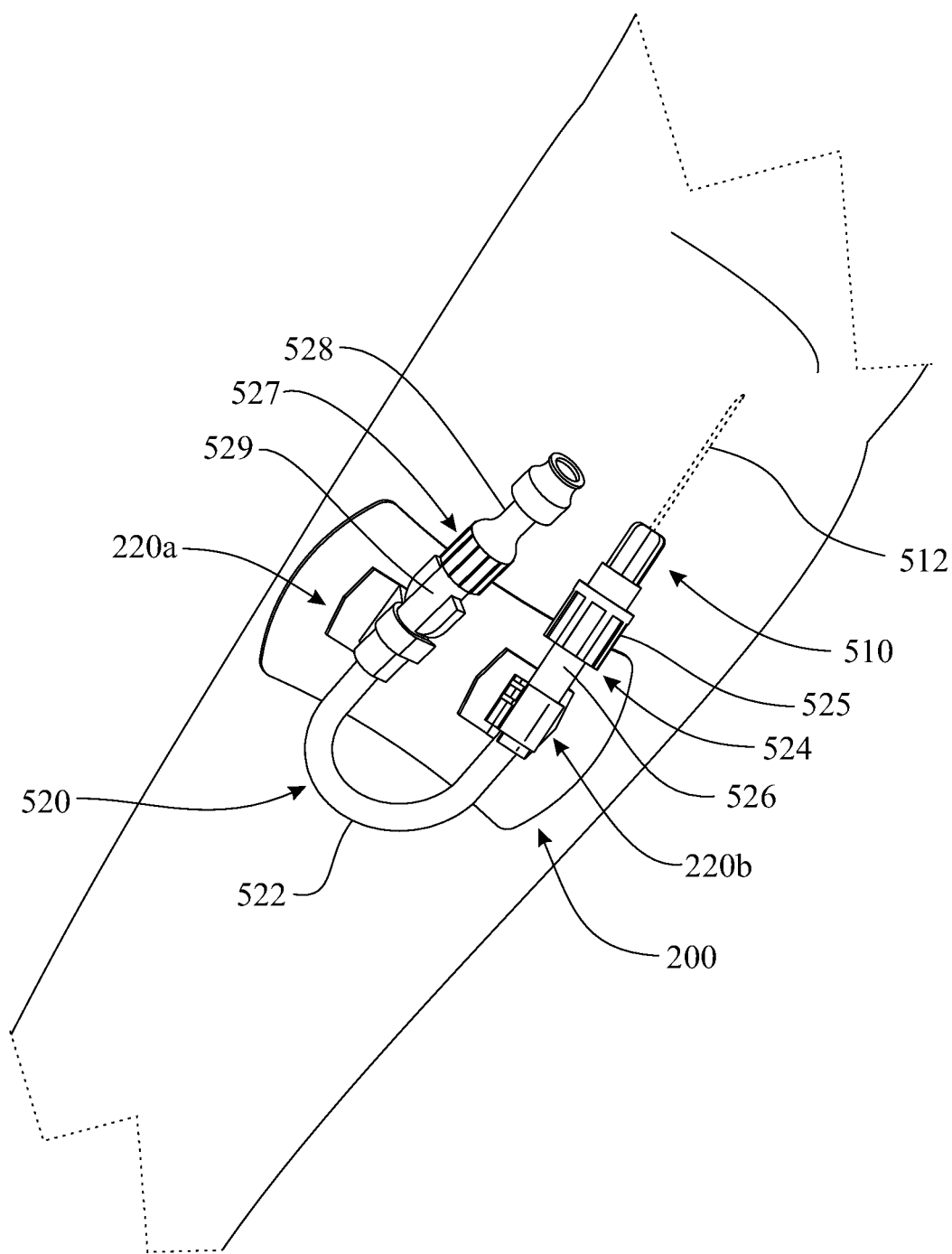
FIG. 8 presents the assembly of FIG. 7 placed on the right arm of a patient.

Having the stabilization device 200 comprise two catheter clipping elements 220a, 220b allows enhancing stabilization of a catheter onto a patient's body. For instance, the illustration of FIG. 7 shows the catheter stabilization device 200 being used to stabilize the assembly formed by catheter 510 and catheter extension element 520 initially introduced in FIG. 4. As shown, one catheter clipping element 220a can be used to clip the rigid neck 529 of the distal terminal adapter 527, and the other catheter clipping element 220b can be used to clip the rigid neck 526 of the proximal terminal adapter 524, in order to keep the distal terminal adapter 527, the proximal terminal adapter 524 and the attached catheter 510 adjacent to the skin.

In addition, as best shown in FIG. 6, the present embodiment is such that the insertion opening 298a of catheter clipping element 220a is oriented horizontally in accordance with a vector 202a forming 180 degrees with transverse direction Y, whereas the insertion opening 298b of catheter clipping element 220b is oriented horizontally in accordance with a vector 202b forming 0 degrees with transverse direction Y. In other words, the catheter clipping elements 220a, 220b of the present embodiment, and the corresponding insertion openings 298a, 298b, are arranged on respective planes 204a, 204b that are perpendicular to said pad top surface, and facing each other. Such faced arrangement of catheter clipping elements 220a, 220b makes it harder for an external element or force to pull on the catheter to cause its removal from the corresponding internal space 290a, 290b, and thus reduces the risk of the catheter undesirably unclipping from either one of the catheter clipping elements 220a, 220b. In this regard, an alternative embodiment is contemplated in which the C-shaped catheter clipping elements are inverted relative to the previous embodiment, such that their insertion openings 298c, 298d (shown in phantom discontinuous format in FIG. 6) do not face one another, while still being arranged on respective planes 204c, 204d that are perpendicular to said pad top surface 212. Such an alternative embodiment facilitates catheter connector insertion and removal through said insertion openings 298c, 298d, to make placing and removing the catheter stabilization device less time-consuming.

Turning again to FIG. 5, it can be observed that the internal space longitudinal axes 292a, 292b are neither parallel to one another nor parallel to the pad top surface 212. Instead, in the depicted embodiment, the internal space longitudinal axis 292a of one catheter clipping element 220a is directed towards the planar pad top surface 212, and the internal space longitudinal axis 292b of the other catheter clipping element 220b is directed away from the planar pad top surface 212. Such a non-parallel arrangement of the elongated resilient clipping body internal spaces 290a, 290b, where one internal space extends towards the patient's skin and the other internal space extends away from the patients skin, is optimum for correctly orienting the catheter. As best understood by FIGS. 7 and 8, the rigid neck 526 of the proximal terminal adapter 524 can be clipped onto one catheter clipping element 220a in a downward orientation, so that the thin flexible tube 512 of the catheter 510 extends downward toward the skin thereby minimizing the risk of unclipping. On the other side, the rigid neck 529 of the distal terminal adapter 527 can be clipped to the other catheter clipping element 220b so that the catheter extension element distal terminal adapter 527 projects outwardly and at a relatively larger distance from the patient's skin, to facilitate manipulation of the distal terminal adapter 527, such as to connect the same to a medicine dispensing machine, bottle, container, receptacle or the like, without contacting the patient's skin.

Figure 9:
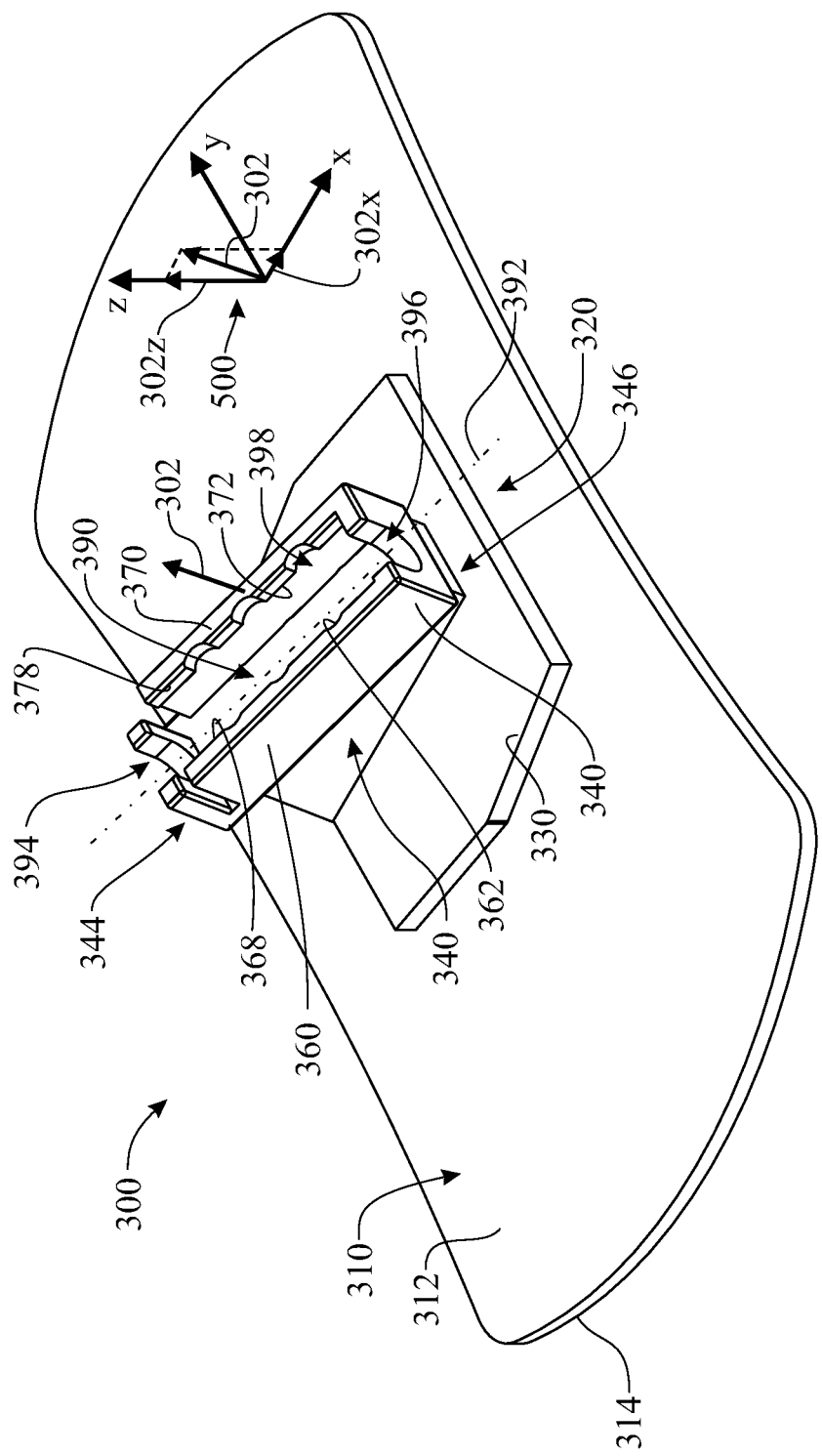
FIG. 9 presents an isometric view of yet another embodiment of the stabilization device in accordance with the invention, comprising a single clipping element having a vertically upward and forward tilted insertion opening.
Figure 10:
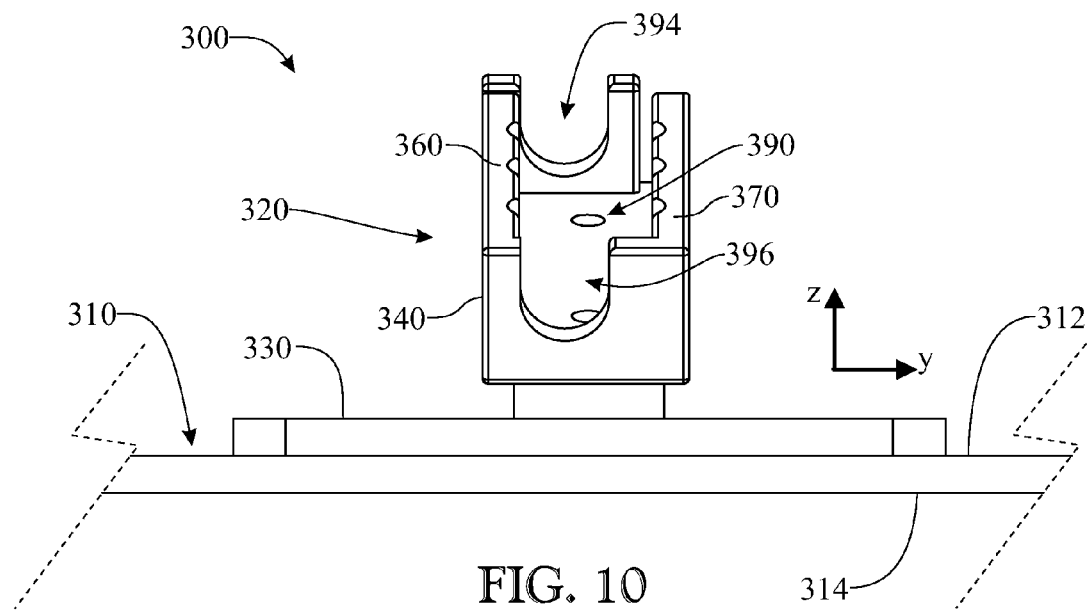
FIG. 10 presents a right side elevation view of the stabilization device of FIG. 9.
Figure 11:
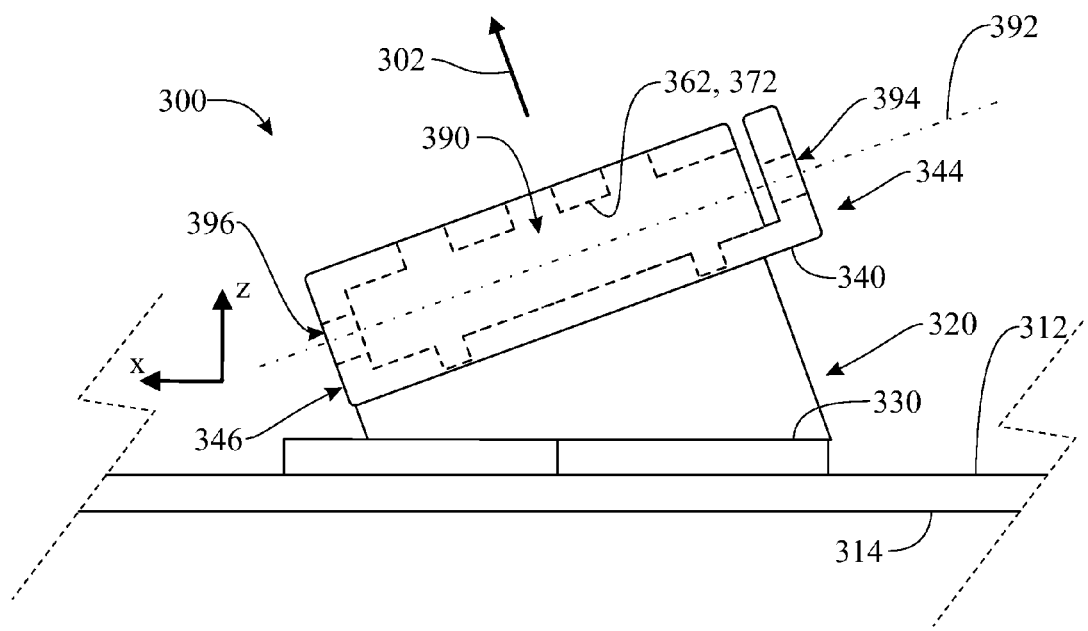
FIG. 11 presents a front elevation view of the stabilization device of FIG. 9.

The illustrations of FIGS. 9 through 11 present another embodiment in accordance with the invention, consisting in a catheter stabilization device 300 comprising a pad 310, the pad 310 having a planar configuration including a top surface 312 and a bottom surface 314. The bottom surface 314 is provided with an anti-allergic adhesive material suitable for removably attaching said bottom 314 surface to skin. The catheter stabilization device 300 further includes a catheter clipping element 320 comprising a base 330, attached to the pad top surface 312, and an elongated resilient clipping body 340 protruding outwardly from the base 330. The clipping body 340 features opposed clipping arms 360, 370 extending in a spaced-apart configuration and resiliently movable relative to one another. Clipping arms 360, 370 comprise respective clipping protrusions 362, 372 for retaining a catheter within an internal space 390 of the clipping body 340. As best shown in FIGS. 9 and 11, the internal space 390 is arranged along an internal space longitudinal axis 392 and extends from a first catheter pass-through opening 394 on a first end 344 of said clipping body 340 and a second catheter pass-through opening 396 on an opposite second end 346 of said clipping body 340. The internal space 390 is accessible through an insertion opening 398 disposed between opposite free ends 368, 378 of said arms 360, 370 and arranged in spatial communication with said opposed first and second catheter pass-through openings 394, 396. Furthermore, the insertion opening 398 is oriented outwardly from the pad top surface 312, in accordance with a vector 302 forming an angle from zero to 180 degrees with said pad top surface 312.

Figure 12:
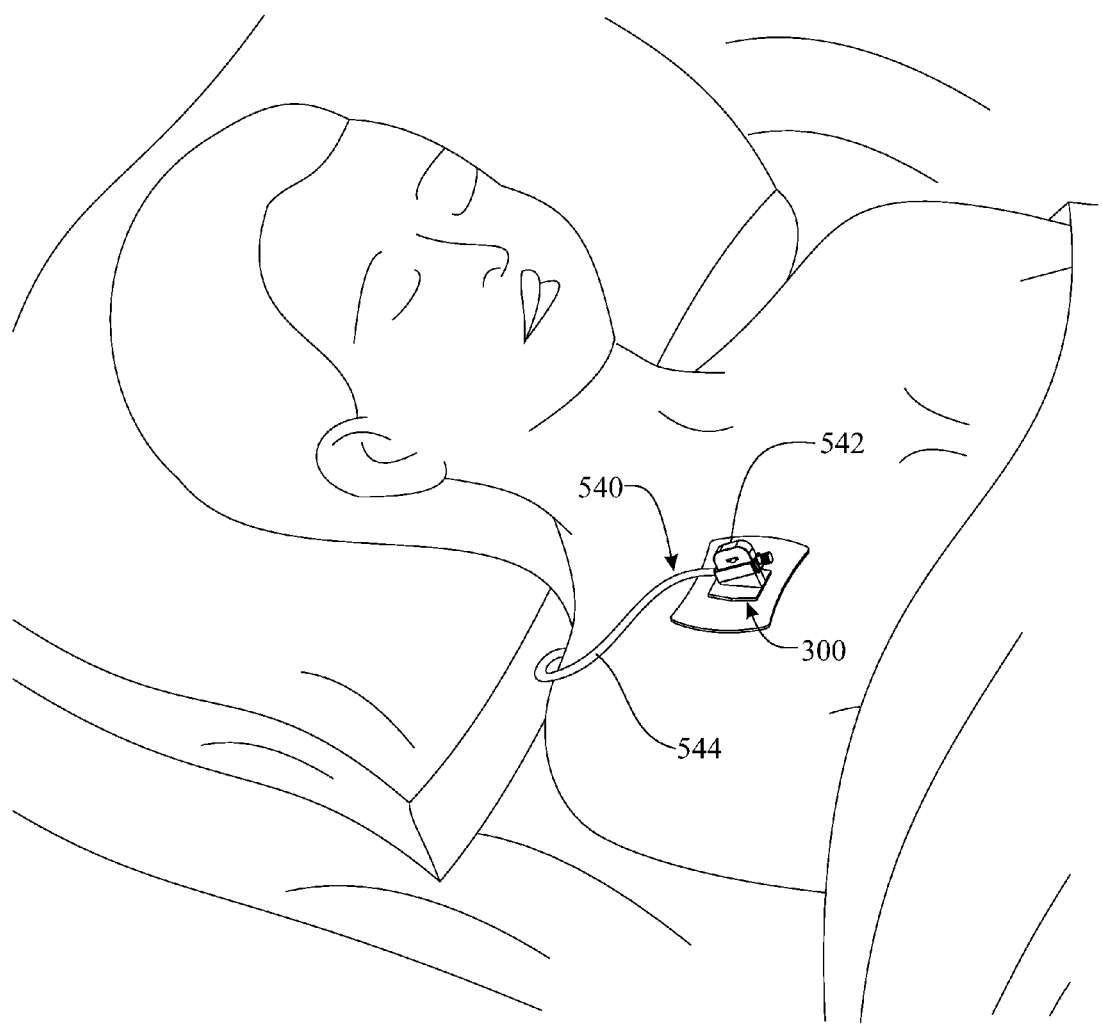
FIG. 12 presents an isometric view of the stabilization device of FIG. 9, shown in use, for stabilizing an epidural catheter extending from an insertion site located on the lower back area of a patient to the skin of a patient's front subclavicular area.

More specifically, the insertion opening 398 of the present embodiment is oriented in accordance with a vector 302 comprising a lateral component 302z as shown in the figure. In other words, the vector 302 and the insertion opening 398 are oriented upwards. Such an upward orientation provides optimum access to the catheter clipping element 320, and allows for a rapid and convenient insertion and removal of the catheter. The present embodiment is especially indicated for medical applications in which a quick stabilization is needed, it not being so relevant to avoid exerting vertically downward forces onto the patient in order to affix the catheter. For example, as shown in FIG. 12, the catheter stabilization device 300 of the present embodiment can be used to stabilize a terminal adapter 542 of an epidural catheter 540, the epidural catheter 540 comprising a thin flexile tube 544 extending into the lower area of the spine of the patient for providing an insertion means for the administration of epidural anesthesia.

In addition to the lateral component 302z, the vector 302 defining the orientation of insertion opening 398 further includes a longitudinal component 302x, as shown in FIG. 9. In other words, the insertion opening 398 is slightly sloped downwards. Such a tilted arrangement allows stabilizing the catheter in a downward orientation towards the skin, thereby reducing the risk of the catheter breaking loose from the catheter stabilization device 300 and guaranteeing that the catheter remains correctly inserted in the body of the patient.

In alternative embodiments of the invention, the shape and/or size of the catheter clipping element and internal space may vary in order to adjust to various catheter connector designs.

In addition, alternative embodiments are contemplated, falling under the scope of the claimed invention, to adapt the device to the left arm, right arm or other body part.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A catheter stabilization device comprising:
    a pad, said pad having a planar configuration extending in longitudinal and transverse directions, said pad including a top surface and a bottom surface, said bottom surface including an adhesive material suitable for removably attaching said bottom surface to skin;
    at least one catheter clipping element, comprising:
        a base, attached to the pad top surface;
        an elongated resilient clipping body protruding from said base, said clipping body comprising opposed clipping arms extending in a spaced-apart configuration and resiliently movable relative to one another, said arms comprising a clipping protrusion;
        an internal space delimited between said arms and configured to partially receive a catheter, wherein said internal space is arranged along an internal space longitudinal axis and extends from a first catheter pass-through opening on a first end of said clipping body and a second catheter pass-through opening on an opposite second end of said clipping body, the internal space longitudinal axis forming an angle other than zero with the planar pad top surface, and wherein said internal space is accessible through an insertion opening disposed between opposite free ends of said arms and arranged in spatial communication with said opposed first and second catheter pass-through openings;
        an elongated stem extending from the base to the elongated resilient clipping body, the stem comprising a first end and an opposed second end, wherein said second end is taller than said first end; wherein said insertion opening is oriented outwardly from said pad top surface, in accordance with a vector forming an angle from zero to 180 degrees with said pad top surface.

2. The catheter stabilization device of claim 1, wherein the elongated resilient clipping body is integrally formed with the stem and the base.

3. The catheter stabilization device of claim 1, wherein the stem is integrally formed with the base, and wherein the elongated resilient clipping body is removably attached to the stem.

4. The catheter stabilization device of claim 1, wherein said insertion opening is arranged on a plane that is perpendicular to said pad top surface.

5. The catheter stabilization device of claim 1, wherein said insertion opening is oriented in an outward direction comprising a lateral component in a lateral direction that is perpendicular to said longitudinal and transverse directions.

6. The catheter stabilization device of claim 5, wherein said outward direction further comprises a longitudinal component in said longitudinal direction.

7. The catheter stabilization device of claim 1, including a single catheter clipping element.

8. The catheter stabilization device of claim 1, including only two catheter clipping elements.

9. The catheter stabilization device of claim 8, wherein the insertion openings of the catheter clipping elements are arranged on respective planes that are perpendicular to said pad top surface, and said insertion openings are oriented facing one another.

10. The catheter stabilization device of claim 9, wherein the internal space longitudinal axis of one catheter clipping element is directed towards the planar pad top surface, and the internal space longitudinal axis of the other catheter clipping element is directed away from the planar pad top surface.

11. The catheter stabilization device of claim 8, wherein the insertion openings of the catheter clipping elements are arranged on respective planes that are perpendicular to said pad top surface, and said insertion openings are oriented oppositely to one another.

12. The catheter stabilization device of claim 11, wherein the internal space longitudinal axis of one catheter clipping element is directed towards the planar pad top surface, and the internal space longitudinal axis of the other catheter clipping is directed away from the planar pad top surface.

13. A catheter stabilization device comprising:
 a pad, said pad having a planar configuration extending in longitudinal and transverse directions, said pad including a top surface and a bottom surface, said bottom surface including an adhesive material suitable for removably attaching said bottom surface to skin;
 at least one catheter clipping element, comprising:
  a base, attached to the pad top surface;
  an elongated resilient clipping body protruding from said base, said clipping body comprising opposed clipping arms extending in a spaced-apart configuration and resiliently movable relative to one another, said arms comprising a clipping protrusion;
  an internal space delimited between said arms and configured to partially receive a catheter, wherein said internal space is arranged along an internal space longitudinal axis and extends from a first catheter pass-through opening on a first end of said clipping body and a second catheter pass-through opening on an opposite second end of said clipping body, the internal space longitudinal axis forming an angle other than zero with the planar pad top surface, and wherein said internal space is accessible through an insertion opening disposed between opposite free ends of said arms and arranged in spatial communication with said opposed first and second catheter pass-through openings;
  an elongated stem extending from the base to the elongated resilient clipping body wherein the stem is integrally formed with the base and the elongated resilient clipping body is removably attached to the stem; wherein
  said insertion opening is oriented outwardly from said pad top surface, in accordance with a vector forming an angle from zero to 180 degrees with said pad top surface.

14. The catheter stabilization device of claim 13, wherein said insertion opening is arranged on a plane that is perpendicular to said pad top surface.

15. The catheter stabilization device of claim 13, wherein said insertion opening is oriented in an outward direction comprising a lateral component in a lateral direction that is perpendicular to said longitudinal and transverse directions.

16. The catheter stabilization device of claim 15, wherein said outward direction further comprises a longitudinal component in said longitudinal direction.

17. The catheter stabilization device of claim 13, wherein the catheter stabilization device includes only two catheter clipping elements, wherein the insertion openings of the catheter clipping elements are arranged on respective planes that are perpendicular to said pad top surface, and said insertion openings are oriented facing one another.

18. The catheter stabilization device of claim 17, wherein the internal space longitudinal axis of one catheter clipping element is directed towards the planar pad top surface, and the internal space longitudinal axis of the other catheter clipping element is directed away from the planar pad top surface.

19. The catheter stabilization device of claim 13, wherein the catheter stabilization device includes only two catheter clipping elements, wherein the insertion openings of the catheter clipping elements are arranged on respective planes that are perpendicular to said pad top surface, and said insertion openings are oriented oppositely to one another.

20. The catheter stabilization device of claim 19, wherein the internal space longitudinal axis of one catheter clipping element is directed towards the planar pad top surface, and the internal space longitudinal axis of the other catheter clipping is directed away from the planar pad top surface.

\* \* \* \* \*